United States Patent
Rasmussen et al.

(10) Patent No.: US 7,477,754 B2
(45) Date of Patent: Jan. 13, 2009

(54) METHOD FOR COUNTERACTING THE OCCLUSION EFFECTS

(75) Inventors: Karsten Bo Rasmussen, Hellerup (DK); Søren Laugesen, Hellerup (DK)

(73) Assignee: Oticon A/S, Smørum (DK)

( * ) Notice: Subject to any disclaimer, the term of this patent is extended or adjusted under 35 U.S.C. 154(b) by 623 days.

(21) Appl. No.: 10/526,229

(22) PCT Filed: Aug. 7, 2003

(86) PCT No.: PCT/DK03/00528

§ 371 (c)(1), (2), (4) Date: Mar. 1, 2005

(87) PCT Pub. No.: WO02/17838

PCT Pub. Date: Mar. 7, 2002

(65) Prior Publication Data
US 2006/0120545 A1    Jun. 8, 2006

(30) Foreign Application Priority Data
Sep. 2, 2002   (DK)  ............................... 2002 01292

(51) Int. Cl.
*H04R 25/00* (2006.01)
*G10K 11/16* (2006.01)
(52) U.S. Cl. ..................................... 381/317; 381/71.2
(58) Field of Classification Search ................ 381/71.1, 381/71.2, 71.6, 312, 313, 314, 315, 317, 381/324, 328; 600/23, 24, 25, 539
See application file for complete search history.

(56) References Cited

U.S. PATENT DOCUMENTS

| | | | |
|---|---|---|---|
| 4,985,925 A | 1/1991 | Langberg et al. | |
| 5,201,006 A | 4/1993 | Weinrich | |
| 5,267,321 A | 11/1993 | Langberg | |
| 5,577,511 A | 11/1996 | Killion | |
| 5,875,254 A | 2/1999 | Hanright | |
| 6,754,359 B1 * | 6/2004 | Svean et al. ................. | 381/313 |
| 2003/0012391 A1 | 1/2003 | Armstrong et al. | |

FOREIGN PATENT DOCUMENTS

| | | |
|---|---|---|
| EP | 1154673 | 11/2001 |
| WO | 02/17838 | 3/2002 |

* cited by examiner

*Primary Examiner*—Brian Ensey
(74) *Attorney, Agent, or Firm*—Dykema Gossett PLLC

(57) ABSTRACT

A method for counteracting the occlusion effect of an electronic device delivering an audio signal to the ear, like a hearing aid or an active ear protector, where the electronic device includes a transmission path with an external microphone or input line which receives a signal from the environment and an signal processor and a receiver which receives processes signal from the signal from the signal processor and delivers sound signals to the ear, whereby an ear piece is inserted into the ear canal and totally or partially blocks the canal. The sound conditions in the cavity between the ear piece and the tympanic membrane are directly or indirectly determined, and whenever condition leading to occlusion problems are determined, the transmission characteristics of the transmission path or the receiver changes in order to counteract the occlusion effect.

9 Claims, 3 Drawing Sheets

METHOD FOR COUNTERACTING THE OCCLUSION EFFECTS

AREA OF THE INVENTION

This invention relates to a method for counteracting the occlusion effect of a sound protector and/or communication device like a hearing aid, whereby an ear piece is inserted into the ear canal and totally or partially blocks the canal.

BACKGROUND OF THE INVENTION

One of the most common complaints of hearing aid users is that their own voice sounds unnatural: boomy, hollow or echoing. Poor sound quality of a person's own voice is also one of the top ten reasons why some hearing aids end up in the drawer. This problem with a person's own voice is very often due to the so-called occlusion effect which occurs because the body-conducted contribution to a person's perception of his/her own voice is trapped in the cavity between the occluding earmold of the hearing instrument and the tympanic membrane. The result is a build-up of sound pressure at low frequencies that may be as much as 30 dB relative to the open-ear. Typically, the occlusion effect has a flat maximum between 80-500 Hz and vanishes above 1 kHz. In the open-ear condition and at the low frequencies considered here, the body-conducted contribution is insignificant compared to the air-conducted contribution. In today's hearing aid dispensing there are basically three ways to address the client's eventual occlusion problem with his/her own voice. First, the earmold (or ITE hearing aid) may be equipped with a vent through which the body-conducted part of his/her own voice can dissipate. Secondly, it has been shown that CIC instruments that are fitted with a seal in the bony part of the ear canal can solve or at least reduce the occlusion problem in many cases. Unfortunately, bony sealed CICs have earned a bad reputation for introducing physical discomfort and are hence rarely dispensed. Thirdly, occlusion problems may be dealt with by counseling—along the lines of "You'll get used to it!". A number of hearing aid users do not manage to get used to it, and they prefer to live with their hearing disorder un-aided.

In U.S. Pat. No. 4,985,925 an active noise reduction based on a negative feed back electro-acoustical system is shown. The system consists of an electronic earplug seated in the concha fossa combining active and passive noise reduction in the quiet zone at the ear, a bilateral transducer circuit which drives a speaker as an acoustical velocity source, a shunt feed back control filter network which improves stability and increases noise reduction, and a combined input noise-filter/feed back system. A typical application is in a noisy environment for hearing protection and for improved communication capability.

SUMMARY OF THE INVENTION

The invention seeks to provide a real solution to the occlusion problem by making use of active hearing aid components.

This is achieved in a method for counteracting the occlusion effect of an electronic device delivering an audio signal to the ear, like a hearing aid or an active ear protector. The electronic device includes a transmission path with an external microphone or input line which receives a signal from the environment and a signal processor and a receiver which receives a signal from the signal processor and delivers sound signals to the ear, whereby an ear piece is inserted into the ear canal and totally or partially blocks the canal. The sound conditions in the cavity between the ear piece and the tympanic membrane are directly or indirectly determined, and whenever conditions leading to occlusion problems are present, the transmission characteristic of the transmission path to the receiver counteracts the occlusion effect.

Keeping track of the sound conditions in the cavity of the occluded ear canal can be done in a number of different ways and the chosen way is not crucial to the invention. Also counteracting the occlusion can be done in a number of different ways by appropriate choice of transmission characteristic of the transmission path from the input to the receiver.

In an embodiment of the invention the conditions leading to occlusion problems are determined by monitoring the activity of the user's own voice, and when a user's own voice activity is detected, the amplification through the signal processor in the frequency region below 1 kHz is reduced. It is the sound transmission through the tissue of the sound from a user's own voice which often leads to the sound pressure build up in the cavity. This can be compensated for by reducing the amplification through the hearing aid in the relevant frequency region below 1 kHz. Hereby, the total sound pressure level in the cavity becomes comfortable. There are a number of ways in which a user's own voice activity can be monitored. One way is to analyze the input signal from the usual microphone and to determine when characteristics which are special to the user's voice are present in the signal. Also, it is possible to use a vibration monitor which monitors the level of vibration in the tissue adjacent to the ear piece. Possibly, the vibration monitor is built into the ear piece.

The sound conditions in the cavity can be monitored by an additional microphone, which is acoustically coupled to the cavity. The signal from the additional microphone is used in a feed back loop to the receiver in order to attenuate the low frequency part of the sound in the cavity. The feed back loop attenuates all low frequency sounds regardless of whether they stem from body functions such as chewing or from own voice or from another source.

When the occlusion problem is solved as described above the attenuation of the low frequency parts of the sound also is applied to the sound, which is received from the surroundings, and this is not desirable. This can be overcome by having the signal processor amplify the low frequency part of the signal from the external microphone in order to compensate for the attenuation of the useful part of the signal from the external microphone or input line. In this way the useful low frequency parts of the signal, which are attenuated by the feed back loop, may be restored in the signal processor. Thus, the user gets the sound from the surroundings with the usual amplification while the occlusion effect is removed or reduced.

According to an embodiment of the invention the feed back loop from the additional microphone is activated by a user's own voice activity. It is not a simple task to determine when to activate the feed back loop, but one safe clue is the activity from the user's own voice. As mentioned earlier, this can be done in many different ways and it is not crucial to the invention which way is chosen here.

In an embodiment of the invention the sound entering the cavity from the tissue and causing the problematic sound levels in the cavity is captured by a viberation pick-up device. The viberation signal is filtered in a filter and combined with the signal which is captured by the external microphone or input line of the device. In this way the cause of the occlusion problem, namely the sound conducted into the ear canal from the surrounding tissue, is used in a direct feed forward manner to eliminate or reduce the low frequency sound built up in the cavity. processor amplify the low frequency part of the signal from the external microphone in order to compensate for the attenuation of the useful part of the signal from the external microphone or input line. In this way the useful low frequency parts of the signal, which are attenuated by the feed back loop, may be restored in the signal processor. Thus the user gets the sound from the surroundings with the usual amplification while the occlusion effect is removed or reduced.

According to an embodiment of the invention feed back loop from the additional microphone is activated by a user's own voice activity. It is not a simple task to determine when to activate the feed back loop, but one safe clue is the activity from the user's own voice. As mentioned earlier, this can be done in many different ways and it is not crucial to the invention which way is chosen here.

In an embodiment of the invention the sound entering the cavity from the tissue and causing the problematic sound levels in the cavity is captured by a vibration pick-up device. The vibration signal is filtered in a filter and combined with the signal which is captured by the external microphone or input line of the device. In this way the cause of the occlusion problem, namely the sound conducted into the ear canal from the surrounding tissues is used in a direct feed forward manner to eliminate or reduce the low frequency sound built up in the cavity.

In a further embodiment of the invention an inward pointing microphone monitors the sound pressure in the cavity. This signal is compared with the signal from the external microphone or input line, and where the comparison result is used to control the shape of the filter. In this way it is assured that the sound inside the ear canal is not allowed to become elevated due to sounds transmission through the tissue of the user and into the ear canal.

DESCRIPTION OF A PREFERRED EMBODIMENT

Figure 1:
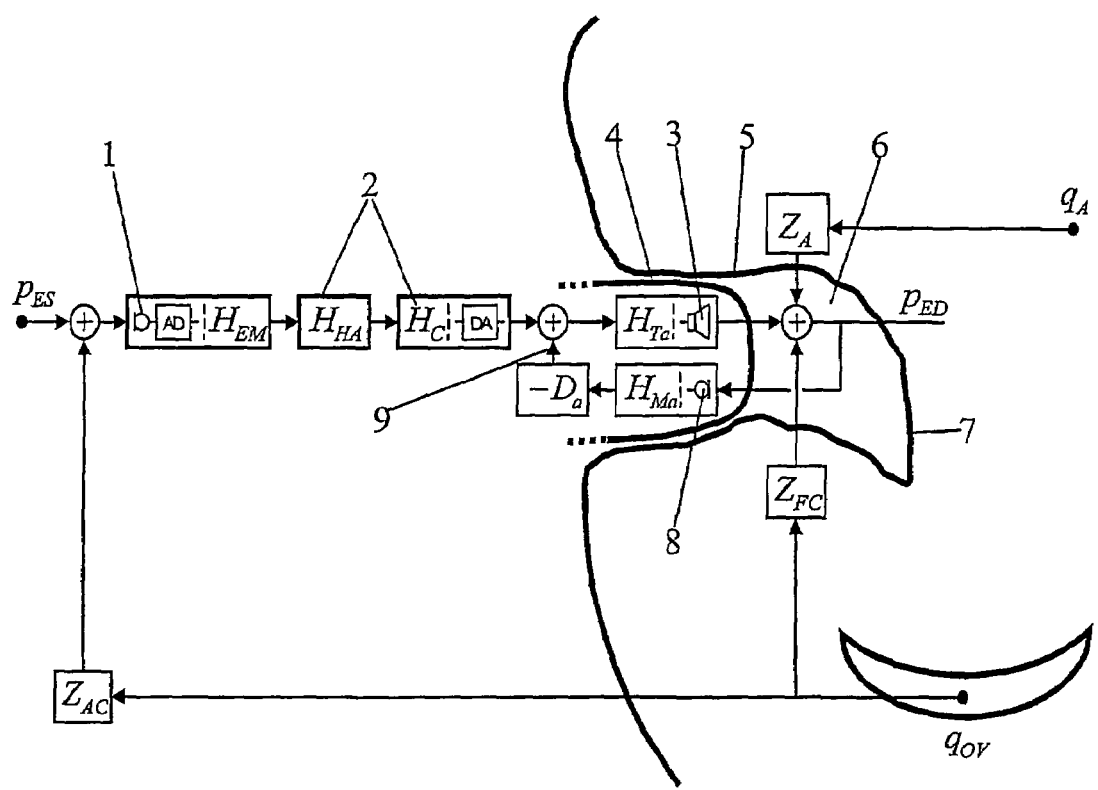
FIG. 1 is a sketch of the feed back approach to anti-occlusion with an internal microphone according to the invention.

The system of FIG. 1 comprises a microphone block comprising microphone 1, AD-converter AD and transfer function HEM. The system further comprises block 2 comprising hearing aid block HHA, additional digital block HC and DA-converter DA. An internal microphone 8 is used in a conventional feed back control system as sketched in FIG. 1. Note that the control loop 9 is assumed to be formed in the analog domain. This is reflected in symbols for the receiver 3 $H_{Ta}$ and internal microphone 8 $H_{Ma}$, transfer functions, where the subscript a denotes a transfer function between two analog signals. Furthermore, the transfer function of the analog feed back controller is denoted by $D_a$ and finally an additional digital block $H_C$ has been added after the hearing aid block $H_{HA}$, as a means of correcting the changes to the amplification characteristic of the hearing aid introduced by the feed back control system. In this set-up $H_C$ also includes the conversion from discrete time signal to analogue signal.

The relation between the source variables and the pressure at the eardrum $P_{ED}$ is $$p_{ED} = \frac{p_{ES} H_{EM} H_{HA} H_C H_{Ta} + q_{OV}}{(Z_{FC} + Z_{AC} H_{EM} H_{HA} H_C H_{Ta}) + q_A Z_A}{1 + D_a H_{Ta} H_{Ma}}. \tag{1}$$

From this equation it is seen that the amount of attenuation, which the body-conducted terms will be subject to is determined by the denominator $1+D_a H_{Ta} H_{Ma}$. Thus, the design of the controller $D_a$ will depend on the desired performance, but is otherwise only dependent on the combined physical transfer function $H_{Ta} H_{Ma}$—in the following shortened to $H_{TMa}$. It is also seen that desired sound $p_{ES}$ will be subjected to the same attenuation as the body-conducted terms. However, this can be counteracted by setting $H_C = 1 + D_a H_{TMa}$, which in turn will mean that the second term in the parantheses following $q_{OV}$ also will assume its original un-controlled value.

Since $H_{TMa}$ will vary considerably between individual subjects and over time on each individual user, the design of $D_a$ will have to be adaptive. Thus, the system sketched in FIG. 1 will have to be extended with an adaptive model of $H_{TM}$, which obviously will have to be digital. Thus the anti-occlusion system will comprise an adaptive discrete time observer from which the transfer function of the analogue controller will be designed. The resulting adjustments to the controller structure will then be implemented as a digitally controllable analogue filter.

In the feed back realization (FIG. 1), the filter $D_a$ is designed according to the requested attenuation at low frequencies due to occlusion, but stability considerations must also be taken into account. Stability is ensured through analysis of the appropriate Nyquist curve for the open loop case and subsequent gain and filtering adjustment.

The combination of signals from the feed back path and from the hearing aid block can be done by means of a receiver equipped with two seperate coils in the electromagnetic system. Hence, as shown in EP patent 1 154 673 the magnetic fields are added within the transducer.

If a vent is present in the hearing aid, the signal coming into the cavity through the vent will also be attenuated by the feed back system. If the vent has a large diameter it will in general decrease the occlusion effect and the anti-occlusion system will be adjusted accordingly or in some cases removed entirely.

Figure 2:
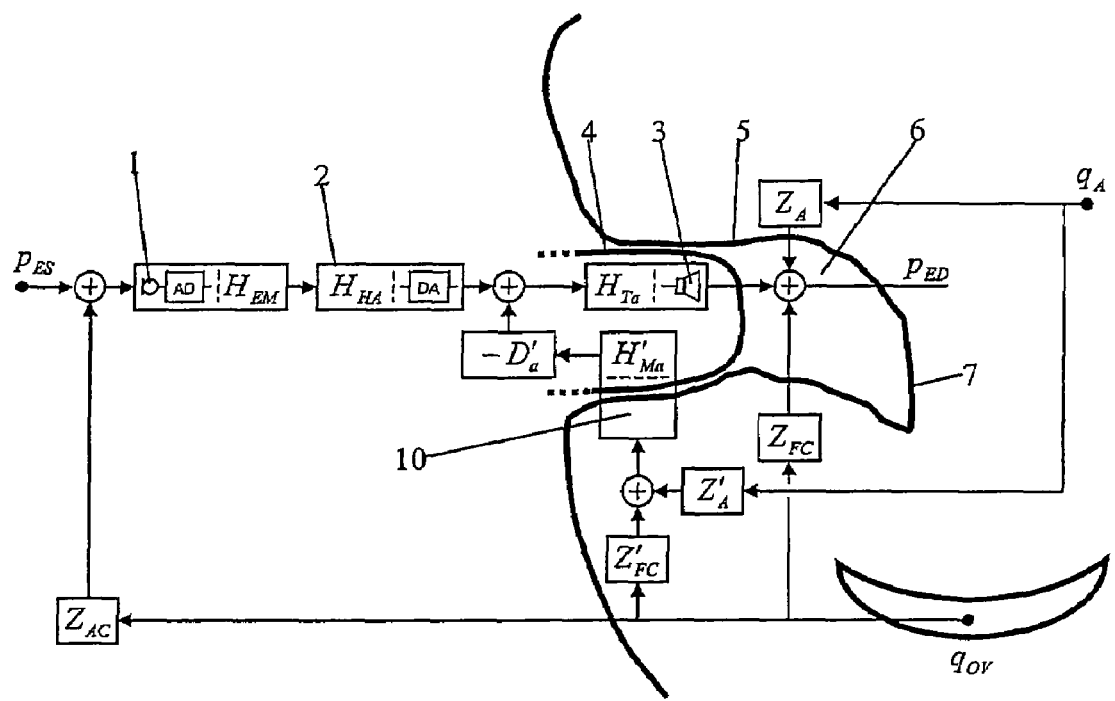
FIG. 2 shows a sketch of the feed forward control approach to anti-occlusion using a vibration pick-up.

In another approach as seen in FIG. 2 an additional electroacoustic transducer 10 is used, which can pick up the vibrations of the soft tissue in the ear canal 5, without picking up either the external sound pressure or the sound pressure generated in the volume 6 between the earmould 4 and the eardrum 7. An idealized block diagram of the control system using such a transducer is seen in FIG. 2. The system of FIG. 2 comprises a microphone block comprising microphone 1, AD-converter AD and transfer function HEM. The system further comprises block 2 comprising hearing aid block HHA and DA-converter DA.

As in the previous section the control is realised in the analogue domain, which means that in this case $H_{HA}$ includes the conversion from discrete time to continuous time. Further, the relations between the own voice volume velocity, $q_{OV}$, and the volume velocity of other internal sources, $q_A$, and the signal picked up by the additional transducer 10 has been denoted by $Z'_{FC}$ and $Z'_A$, respectively, the (analogue) transfer function of the alternative transducer has been denoted by $H'_{Ma}$, and the controller by $D'_a$. The relation between the source signals and the sound pressure at the eardrum is $$p_{ED} = \quad (2)$$
$$p_{ES}H_{EM}H_{HA}H_{Ta} + q_{OV}(Z_{FC} - Z'_{FC}H'_{Ma}D'_aH_{Ta} + Z_{AC}H_{EM}H_{HA}H_{Ta}) +$$
$$q_A(Z_A - Z'_A H'_{Ma}D'_a H_{Ta}).$$

It is seen that occlusion can be reduced by adjustment of the controller $D'_a$ so that the $q_{OV}$ term is made sufficiently small.

In this idealised description it is clear that a couple of potential signal paths have been left out of the picture. The most important one is the path from the sound pressure at the eardrum to the signal picked up by the vibration pick-up. If this path is significant the system will be a hybrid feed forward/feed back system, which will be more difficult to design. A probably much less important contribution is that from the external sound pressure to the signal picked up by the vibration pick-up.

The above described feed forward approach may be supplemented by a microphone 8 measuring the sound pressure in the cavity 6 as in the feed back approach (se FIG. 1). In relation to the feed forward approach, the transducer provides an error signal used for dynamic adjustment of the controller $D'_a$ for minimum deviation between sound pressure in the cavity and the desired signal at the eardrum which will probably be, $$p_{ED} = p_{ES}H_{EM}H_{HA}H_{Ta} + q_{OV}Z_{AC}H_{EM}H_{HA}H_{Ta}$$

Hence, the additional internal microphone makes it possible to use an adaptive filter approach taking changes in transfer functions through human tissue into account. These changes could stem from facial expressions, jaw movements, temperature changes etc.

The feed forward embodiment of the anti-occlusion system has a transducer which provides a measure of the tissue vibrations and since this vibration contribution is known, an equivalent signal can be emitted in opposite phase from the receiver in order to cancel the influence of this signal in the cavity.

The feed forward embodiment above may also be implemented using digital signal processing, such that the signal from the vibration pick-up is converted with its own AD converter and the DA converter in FIG. 2 instead becomes part of $H_{Ta}$.

In another embodiment the above mentioned adaptive adjustment is not included and the internal microphone is not included.

Figure 3:
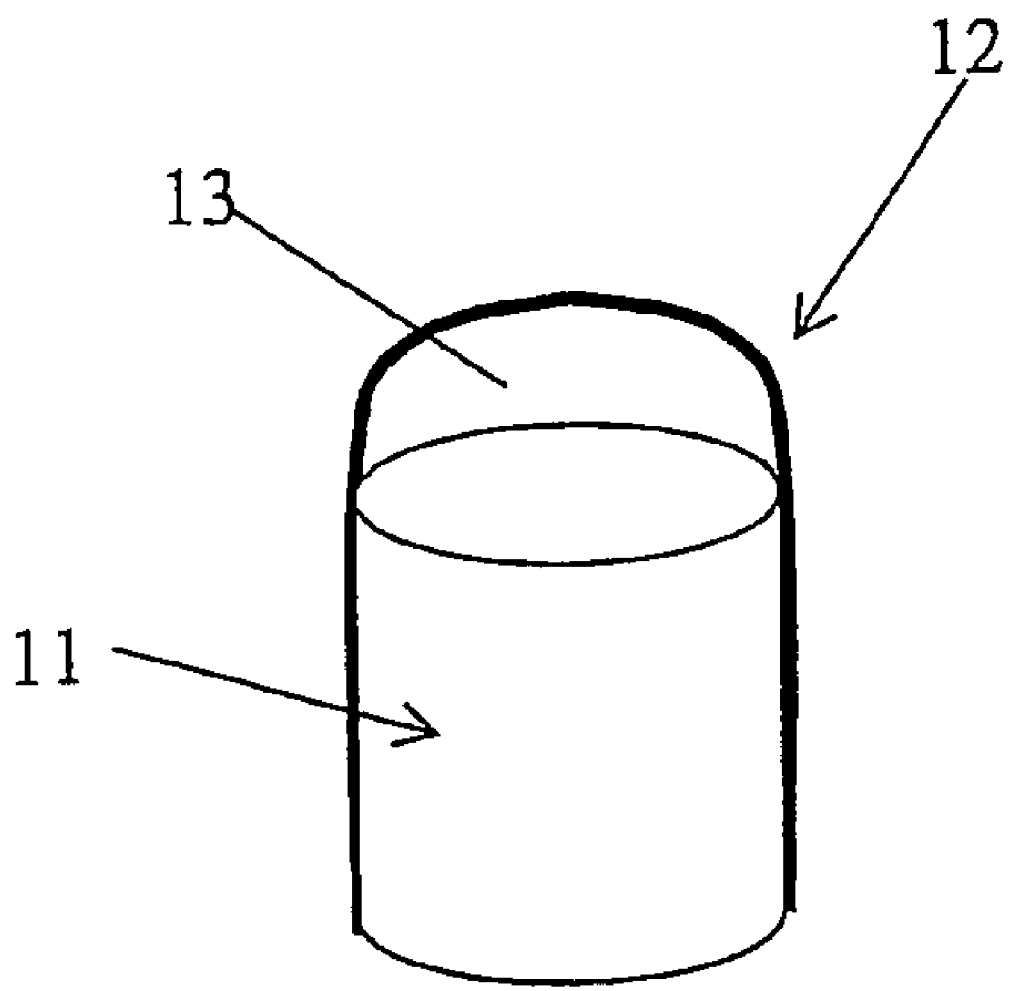
FIG. 3 is a schematic representation of the vibration pick-up.

In FIG. 3 a transducer 10 for picking up body conducted sound is outlined. The transducer 10 is constructed on the basis of a cylindrically shaped Knowles FG microphone 11. A Knowles FG3453-C with a cut-off frequency of 125 Hz is used. The transducer 10 consists of a microphone 11 equipped with an airtight cap 12 or bell of fluoride rubber. The rubber bell is 1.5 mm high measured from the top of the microphone and 0.15 mm thick at the top. The design provides good vibration sensitivity when suitable physical contact exists between the rubber and the surrounding tissue. This choice represents a very compact and yet simple transducer, and it ensures good sensitivity and a high degree of attenuation of air-borne sound. The transducer is mounted so that good contact to the skin is provided while leaving sufficient air in the cavity 13 in front of the microphone in order to avoid rectifying the signal.

The invention claimed is:

1. Method for counteracting the occlusion effect of an electronic device delivering an audio signal to an ear, wherein the electronic device comprises a transmission path with an external microphone or input line which receives a signal $p_{ES}$ from the environment, a signal processor and a receiver which receives a processed signal from the signal processor and delivers sound signals to the ear, whereby an ear piece is inserted into the ear canal and totally or partially blocks the canal whereby the sound conditions in a cavity between the ear piece and the tympanic membrane are directly or indirectly determined, and whenever conditions leading to occlusion problems are determined, transmission characteristic of the transmission path to the receiver counteracts the occlusion effect, monitoring the sound conditions in the cavity by an additional microphone which is acoustically coupled to the cavity, using the signal from the additional microphone in a feed back loop to the receiver in order to attenuate the low frequency part of the sound in the cavity, and forming the feed back loop to the receiver in the analogue domain.

2. Method as claimed in claim 1, including monitoring conditions leading to occlusion to determine activity of the user's own voice, and when a user's own voice activity is detected, reducing amplification through the signal processor in the frequency region below 1 kHz.

3. Method as claimed in claim 1, including amplifying a low frequency part of the signal from the external microphone in the signal processor in order to compensate for the attenuation of a useful part of the signal from the external microphone or input line.

4. Method as claimed in claim 1, including activating the feed back loop from the additional microphone by a user's own voice activity.

5. Method as claimed in claim 1, whereby the sound entering the cavity from the tissue and causing the occlusion sound levels within the cavity is captured by a vibration pick-up, and where the vibration signal is filtered in a filter $D'_a$ and combined with the signal which is captured by the external microphone or input line of the device.

6. Method as claimed in claim 5, including monitoring the sound pressure in the cavity with an inward pointing microphone producing a signal, comparing said signal with the signal from the external microphone or input line, and using the comparison to control the shape of the filter $D'_a$.

7. Method as claimed in claim 1, whereby the detection of a user's own voice activity is carried out by a vibration pick-up in contact with a body portion of the user.

8. Method as claimed in claim 1, wherein the transmission path comprises a conversion from discrete time signals to analogue signals to allow the feed back loop to the receiver to be formed in the analogue domain.

9. Method as claimed in claim 1, wherein stability considerations are taken into account through analysis of the appropriate Nyquist curve for the open loop case and subsequent gain and filtering adjustment.

* * * * *